US012725685B2

(12) United States Patent
Schurzig et al.

(10) Patent No.: US 12,725,685 B2
(45) Date of Patent: Sep. 1, 2026

(54) PATIENT-SPECIFIC INDIVIDUALIZATION OF AN ELECTRODE ARRAY FOR A COCHLEAR IMPLANT

(71) Applicant: MED-EL Elektromedizinische Geräte Ges.m.b.H., Innsbruck (AT)

(72) Inventors: Daniel Schurzig, Hannover (DE); Cornelia Batsoulis, Hannover (DE); Pavel Mistrik, Hall in Tirol (AT)

(73) Assignee: MED-EL Elektromedizinische Geräte Ges.m.b.H., Innsbruck (AT)

( * ) Notice: Subject to any disclaimer, the term of this patent is extended or adjusted under 35 U.S.C. 154(b) by 218 days.

(21) Appl. No.: 18/832,543

(22) PCT Filed: Jan. 30, 2023

(86) PCT No.: PCT/EP2023/052115
§ 371 (c)(1),
(2) Date: Jul. 24, 2024

(87) PCT Pub. No.: WO2023/144361
PCT Pub. Date: Aug. 3, 2023

(65) Prior Publication Data

US 2025/0095805 A1 Mar. 20, 2025

(30) Foreign Application Priority Data

Jan. 31, 2022 (EP) .................................... 22154393

(51) Int. Cl.
*G16H 10/60* (2018.01)
*A61N 1/05* (2006.01)
(Continued)

(52) U.S. Cl.
CPC ........... *G16H 10/60* (2018.01); *A61N 1/0541* (2013.01); *B29C 33/301* (2013.01); (Continued)

(58) Field of Classification Search
None
See application file for complete search history.

(56) References Cited

U.S. PATENT DOCUMENTS

2022/0285005 A1* 9/2022 Noble .................. A61B 5/0536

FOREIGN PATENT DOCUMENTS

WO WO-2021053045 A1 * 3/2021 ......... A61N 1/36039

OTHER PUBLICATIONS

Helpard et al., "An Approach for Individualized Cochlear Frequency Mapping Determined from 3D Synchrotron Radiation Phase-Contrast Imaging," IEEE Transactions on Biomedical Engineering, vol. 68, No. 12, pp. 3602-3611 (2021), 10 pages. (Year: 2021).*

(Continued)

*Primary Examiner* — Andrew H Lam
(74) *Attorney, Agent, or Firm* — Barclay Damon LLP

(57) ABSTRACT

The present invention aims at providing a cochlear implant, in particular an electrode array of a cochlear implant, adapted to the specific requirements of a given patient in an improved manner, possibly taking into account the specific cochlea anatomy and hearing assistance needs of each individual patient. A first aspect of the invention refers to a method for determining a geometry, in particular a patient-specific geometry, of an electrode array for a cochlear implant for a patient. The method comprises computing a predicted arrangement of the electrode array within the cochlea of the patient based on: i) patient-specific data about the geometry of the cochlea of the patient and/or of a part thereof, and ii) a predefined geometric relation between the geometry of the cochlea of the patient (or of a part thereof) and the predicted arrangement of the electrode array when received within the cochlea of the patient.

20 Claims, 7 Drawing Sheets

(51) Int. Cl.
*B29C 33/30* (2006.01)
*B29C 33/38* (2006.01)
*B29L 31/00* (2006.01)
*G16H 40/40* (2018.01)

(52) U.S. Cl.
CPC ......... *B29C 33/3835* (2013.01); *G16H 40/40* (2018.01); *B29L 2031/7546* (2013.01)

(56) References Cited

OTHER PUBLICATIONS

Schurzig et al., "A Novel Method for Clinical Cochlear Duct Length Estimation toward Patient-Specific Cochlear Implant Selection," OTO Open [online] vol. 2, No. 4, (2018), 8 (Year: 2018).*
International Search Report and Written Opinion in Application No. PCT/EP2023/052115 dated Mar. 21, 2023, 10 pages.
Helpard et al., "An Approach for Individualized Cochlear Frequency Mapping Determined from 3D Synchrotron Radiation Phase-Contrast Imaging," IEEE Transactions on Biomedical Engineering, vol. 68, No. 12, pp. 3602-3611 (2021), 10 pages.
Schurzig et al., "A Novel Method for Clinical Cochlear Duct Length Estimation toward Patient-Specific Cochlear Implant Selection," OTO Open [online] vol. 2, No. 4, Retrieved from the Internet <URL:https://onlinelibrary.wiley.com/doi/fu11-XML/10.1177/2473974X18800238> [retrieved on Mar. 13, 2023] (2018), 8 pages.

* cited by examiner

PATIENT-SPECIFIC INDIVIDUALIZATION OF AN ELECTRODE ARRAY FOR A COCHLEAR IMPLANT

CROSS-REFERENCE TO RELATED APPLICATIONS

This application is the national phase entry of International Patent Application No. PCT/EP2023/052115, filed Jan. 30, 2023, which claims the benefit of European Patent Application No. 22154393.7, filed Jan. 31, 2022, the disclosures of which are incorporated herein by reference in their entirety.

FIELD OF THE INVENTION

The invention is in the field of cochlear implants. In particular, the invention refers to a method and a system for determining a geometry of an electrode array for a cochlear implant and to a related method for manufacturing an electrode array for a cochlear implant.

BACKGROUND OF THE INVENTION

As shown in FIG. 1, sounds are transmitted by a human ear from the outer ear 101 to the tympanic membrane (eardrum) 102, which moves the bones of the middle ear 103 (malleus, incus, and stapes) that vibrate the oval window and round window openings of the cochlea 104. The cochlea 104 is a long fluid-filled duct wound spirally about its axis for approximately two and a half turns (9000). It includes an upper channel known as the scala vestibuli and a lower channel known as the scala tympani, which are connected by the cochlear duct. The scala vestibuli and the scala tympani are delimited by their internal walls. The cochlea 104 forms an upright spiraling cone with a center called the modiolus where the spiral ganglion cells (SGCs) of the auditory nerve 113 reside. These SGCs have axons projecting in one direction to the cochlear nucleus in the brainstem and they project in the other direction to the Organ of Corti. In response to received sounds transmitted by the middle ear 103, sensory hair cells in the cochlea 104 function as transducers to convert mechanical motion and energy into electrical discharges in the auditory nerve 113. These discharges are conveyed to the cochlear nucleus and patterns of induced neural activity in the nucleus are then conveyed to other structures in the brain for further auditory processing and ultimately perceiving the neural signals as sound.

Hearing is impaired when there are problems in the ability to transduce external sounds into meaningful action potentials along the neural substrate of the cochlea 104. To improve impaired hearing, auditory prostheses have been developed. When the impairment is associated with the cochlea, hearing impairment can be addressed by a cochlear implant (Cl), a cochlear implant with an implanted stimulation electrode can electrically stimulate auditory nerve tissue with small currents delivered by multiple electrode contacts 112 distributed along an electrode array 110 that is inserted into the scala tympani of the cochlea 104 of the patient.

Due to the variability introduced by the specific anatomy of each individual patient, cochlear implants display a variability of implantation outcomes. Every cochlea is unique and it differs in its size, shape, number of turn and as well in its anatomy from other cochleae. Consequently, aspects such as postoperative residual hearing, music appreciation and speech perception can vary quite substantially between patients.

One approach for facilitating patient-specific cochlear implantation is the production and commercialisation of a large portfolio of electrode arrays among which to choose for each patient. This approach allows for some degree of individualisation by choosing, among the available types of electrode array, an electrode array having the most suitable geometry for a given patient. However, the number of off-the-shelf electrode arrays available is always limited and hence mostly unable to optimally satisfy the individual needs of a specific patient.

Another approach that is currently being investigated is based on the adjustment of the specific frequency bands associated by a control software of the cochlear implant to each electrode contact of the electrode array taking into account the individual cochlear anatomy of a given patient. However, this adjustment can only be done within certain limitations caused by the limitations of the filter banks used by the cochlear implant and to the position of the already implanted electrode array. Therefore, optimal individualisation cannot be achieved.

Thus, there is room for technical improvement regarding the individualisation of cochlear implants for a specific patient.

SUMMARY OF THE INVENTION

The present invention aims at providing a cochlear implant, in particular an electrode array of a cochlear implant, adapted to the specific requirements of a given patient in an improved manner, possibly taking into account the specific cochlea anatomy and hearing assistance needs of each individual patient. This problem is solved by a method according to claim 1, by a system according to claim 14 and by an electrode array manufacturing according to the method of claim 20. Preferred embodiments of the invention are defined in the dependent claims.

A first aspect of the invention refers to a method for determining a geometry, in particular a patient-specific geometry, of an electrode array for a cochlear implant for a patient. The electrode array may preferably be a flexible electrode array having an elongated shape and comprising a plurality of electrode contacts arranged along a longitudinal extension of the electrode array.

The method, which may in particular be a computer implemented method, comprises computing a predicted arrangement of the electrode array within the cochlea of the patient based on:

i. patient-specific data about the geometry of the cochlea of the patient and/or of a part thereof, in particular of the scala tympani and/or of an inner or outer inner wall thereof or of a lateral wall of the cochlea, usually referred to as "LW" and corresponding to an outer wall or outer bony edge of the cochlea, in particular at the level of the basilar membrane or of the organ of corti; and ii. a predefined geometric relation between the geometry of the cochlea of the patient (or of a part thereof, for example of said lateral wall LW of the cochlea of the patient), and the predicted arrangement of the electrode array when received within the cochlea of the patient.

The method further comprises determining (predicting) the geometry of the electrode array based on the computed predicted arrangement of the electrode array within the cochlea of the patient.

The patient-specific data about the geometry of the cochlea of the patient reflects the real geometry, in particular the real 3D geometry, for example the real size, shape, number of turns and/or anatomy, of the cochlea of the patient and/or of a part thereof, in particular a spiral path of the cochlea of the patient and/or of said part thereof. The patient-specific data about the geometry of the cochlea of the patient models the geometry of the cochlea of the patient. Reference will be made here to geometric and anatomic characteristics "of the cochlea" and the skilled person shall understand that, unless otherwise specified, such references must be understood as referring not only to characteristic of the cochlea as a whole, but possibly referring to corresponding characteristics of said part of the cochlea of the patient. Said part of the cochlea of the patient may, be or correspond to the scala tympani or to an inner or outer internal wall thereof, for example to the basilar membrane, which is arranged on the outer inner wall of the scala tympani and/or for example to the previously mentioned lateral wall LW of the cochlea of the patient.

Thus, the patient-specific data about the geometry of the cochlea of the patient may for example be or comprise patient-specific data about the geometry (e.g. real size, shape, number of turns and/or anatomy) of the scala tympani of the patient, in particular of an outer or inner internal wall of the scala tympani of the patient, for example of the basilar membrane of the patient. As a further example, the patient-specific data about the geometry of the cochlea of the patient may for example be or comprise patient-specific data about the geometry (e.g. real size, shape, number of turns and/or anatomy) of the previously mentioned lateral wall LW of the cochlea of the patient.

The patient-specific data is specifically related to an individual patient and may for example be data obtained by an imaging technique such as computer tomography (CT), in particular cone beam computed tomography (CBCT). The lateral wall LW of the cochlea can be typically distinguished in clinical CBCT images.

According to some embodiments, the method may comprise obtaining the patient-specific data about the geometry of the cochlea of the patient using an imaging technique, preferably computer tomography, more preferably cone beam computed tomography (CBCT). The method may comprise performing a corresponding imaging process or obtaining the patient-specific data from an external input device such as a data storage device or an imaging device. For example, the patient-specific data about the geometry of the cochlea of the patient may be obtained using segmentation with OsiriX MD to reconstruct the spiral path followed by the cochlea of the patient or by a part thereof, in particular by the previously mentioned lateral wall LW of the cochlea, as described by D. Schurzig et al. in "Cochlea Helix and Duct Length Identification—Evaluation of Different Curve Fitting Techniques," Cochlear Implants Int. 19(5), pp. 268-83, 2018.

The patient-specific data may reflect volumetric geometry of the cochlea of the patient and/or of said part thereof. Thus, the patient-specific data about the geometry of the cochlea of the patient may reflect, not only a 3D spiral path followed by the cochlea of the patient or by the respective part thereof, for example by lateral wall LW of the cochlea of the patient, but may also reflect or estimate the geometry of the cochlea of the patient and/or of a part thereof (possibly a different one) in dimensions perpendicular to said 3D spiral path. In other words, the patient-specific data about the geometry of the cochlea of the patient may also reflect size, shape and/or extension of cross-sections of the cochlea perpendicular to said 3D spiral path. Thus, the patient-specific data may reflect an inner volume of the cochlea of the patient and/or of a part thereof.

In preferred embodiments, the method may comprise generating the patient-specific data about the geometry of the cochlea of the patient as volumetric data based on patient-specific data about a spiral path of the cochlea of the patient or of a part thereof, i.e. a 3D spiral path of the cochlea of the patient or of a part thereof (e.g. by the lateral wall LW of the cochlea), and on empirical data about cross-sectional areas of a human cochlea or of a part thereof perpendicular to a corresponding spiral path of the human cochlea for different insertion angles.

"Insertion angle" is a term familiar to the skilled person and refers to an angular parameter characterising a location within the cochlea of the patient by an angle measured with respect to an origin line joining the modiolus and the center of the round window, such that the center of the round window corresponds to an insertion angle of 0°, an insertion angle of 360° corresponds to a position along the spiral path of the cochlea at which the cochlea has completed a full turn, and a maximal insertion angle corresponds to the apical end of the cochlea.

For each insertion angle value along the spiral path of the cochlea of the patient, a corresponding empirically determined, e.g. statistically averaged, cross-section of the human cochlea (for example averaged for a given test population not necessarily including the patient) corresponding to the same insertion angle value along the spiral path of a statistically modelled human cochlea may be used to add estimated cross-sectional information to the real patient-specific path information encoded in the patient-specific data about the spiral path of the cochlea.

According to this embodiment, the patient-specific data about the geometry of the cochlea of the patient may be generated based on patient-specific data reflecting the spiral path followed in 3D space by a 3D line within cochlea, for example by the lateral wall LW of the cochlea of the patient, and on empirical data that enhance the description of said spiral path to a full volumetric description by incorporating the empirical data, which may be or comprise statistical data obtained from a test population. The full volumetric structure of the cochlea of the patient or of the part thereof can thereby be obtained by adding to the information about the spiral path followed in 3D space by a 3D line of the cochlea of the patient the cross-sectional information encoded in the empirical data corresponding to cross-sectional planes perpendicular to a corresponding spiral path of a statistically modelled human cochlea at corresponding insertion angles.

Notably, a part of the cochlea of the patient described and/or covered by the patient-specific data about the geometry of the cochlea of the patient needs to not correspond, overlap or be comprised in a part of the human cochlea described and/or covered by the empirical data. For example, the patient-specific data about the geometry of the cochlea of the patient may correspond to a 3D spiral path followed by lateral wall LW of the cochlea of the patient and the empirical data may correspond to the average anatomies of the human scala tympani, as described by D. Schurzig et al. in "Uncoiling the Human Cochlea—Physical Scala Tympani Models to Study Pharmacokinetics Inside the Inner Ear," *Life* 11(5): 373, 2021.

The geometry of the cochlea of the patient (or of a part thereof, for example of the lateral wall LW of the cochlea) is known from the patient-specific data about the geometry of the cochlea of the patient. The arrangement of the electrode array when received within the cochlea of the patient is a priori unknown. The predefined geometric relation allows predicting the predicted arrangement of the electrode array when inserted within the cochlea of the patient by assuming that a geometric relation between the real arrangement of the electrode array once it is received within the cochlea of the patient and the geometry of the cochlea of the patient, which is modelled by the patient-specific data, will correspond to the predefined geometric relation, which may for example be obtained from empirically generated statistical data set and needs not be patient-specific.

The predicted arrangement of the electrode array may describe the arrangement within the cochlea of the patient, for example within the scala tympani of the patient, of a center-line of the electrode array and/or of a full volumetric representation of the electrode array, for example by incorporating information about a cross-section of the electrode array, possibly as a function of length.

According to some embodiments, the predefined geometric relation may correspond to a predefined distance between the electrode array, in particular a centre-line thereof, and a spiral path of the cochlea of the patient or of a part thereof, preferably a spiral path of (followed by) the lateral wall LW of the cochlea of the patient or by an inner or outer internal wall of the scala tympani of the patient. The predefined distance may for example be assumed to be a constant distance independent of insertion angle, for instance a constant distance of 0.35 mm according to the model by Alexiades et al. in "Method to estimate the complete and two-turn cochlear duct length," *Otology & Neurotology*, vol. 36, no. 5, pp. 904-7, 6 2015. However, the predefined distance may be also a dependent on insertion angle, i.e. a distance d expressed as a function d(IA) of insertion angle IA. Such a function, which may be specific of a given electrode array, may be obtained from empirically generated statistical data, for example as described by Sacher et al. in "On the Intracochlear Location of Straight Electrode Arrays After Cochlear Implantation: How Lateral Are Lateral Wall Electrodes?," Otol Neurotol 42(2), pp. 242-250, 2021.

In preferred embodiments, the predicted arrangement of the electrode array within the cochlea of the patient may be computed assuming:

- that the electrode array, in particular a centre-line thereof, is arranged at a first predetermined distance from a spiral path of the cochlea of the patient or of a part thereof in a horizontal direction parallel to a shortest distance from said spiral path of the cochlea of the patient or from said part thereof to the modiolus of the patient; and
- that the electrode array, in particular the centre-line thereof, is arranged within the scala tympani of the patient at a second predetermined distance from the spiral path of the cochlea of the patient or of a part thereof in a vertical direction parallel to the modiolus of the patient.

Thereby, a predicted position of the electrode array in a cross-sectional plane perpendicular to the spiral path of the cochlea, which may for example be a spiral path of the lateral wall LW of the cochlea of the patient, is obtained by projecting the spiral path in said horizontal direction by the first predetermined distance and in said vertical direction by the second predetermined distance. This provides a systematic manner of computing the predicted arrangement of the electrode array within the cochlea of the patient from the spiral path of the cochlea of the patient or of said part thereof, which may be encoded in the patient-specific data about the geometry of the cochlea of the patient. The first predetermined distance may correspond to the previously described predefined distance, in particular to a constant distance independent of insertion angle, for instance to a constant distance of 0.35 mm according to the previously cited model by Alexiades et al. or to a predefined distance d expressed as a function d(IA) of insertion angle IA, possibly associated to a given type of electrode array, obtained from empirically generated statistical data as described in the previously cited reference of Sacher et al.

The second predetermined distance may correspond to a predetermined fraction of the separation distance between an upper sidewall of the scala tympani of the patient adjacent to the scala vestibuli and a lower sidewall of the scala tympani opposite the upper sidewall of the scala tympani in said vertical direction. The predetermined fraction, which may for example be 0.3, 0.4, 0.5, 0.6 or 0.7, corresponds to a height of the predicted cross-sectional position of the electrode arrangement over the lower sidewall of the scala tympani expressed as a fraction of a height of the upper sidewall of the scanner tympani over the lower sidewall of the scala tympani at the horizontal position defined by the first predetermined distance.

According to preferred embodiments, the determining the geometry of the electrode array may comprise determining a length of the electrode array. The length of the electrode array correlates with the maximal insertion angle to which the electrode array is insertable into the cochlea of the patient and is hence related with the range of tonotopic positions along the cochlea of the patient that are to receive electrical stimulation. In embodiments in which the predefined geometric relation corresponds to a predefined distance between the electrode array and the spiral path of the cochlea of the patient or of a part thereof, the predefined geometric relation, for example the insertion angle dependent distance d(IA), may be specific for a given length of the electrode array, i.e. may be obtained from empirically generated statistical data obtained for test electrode arrays having a length corresponding to the length of the electrode array.

In preferred embodiments of the invention, determining the geometry of the electrode array may comprise determining a position of one or more electrode contacts, in particular stimulation electrode contacts connectable to a speech processor for providing electrical stimulation, along the electrode array based on the computed predicted arrangement of the electrode array within the cochlea of the patient and based on patient-specific data about a neural survival status of the cochlea of the patient.

Neural survival refers herein to a property indicating healthy and/or functional auditory nerve and/or cochlear tissue preserving sufficient neural structures and ability to be activated or discharge when stimulated with an electrical stimulus corresponding to a sound signal so as to convey a neural signal to other neural structures for further auditory processing and for ultimately perceiving the neural signal as sound in the brain. A neural survival status is a characterisation of the neural survival of the cochlea of the patient, and may for example be a function dependent on insertion angle to reflect neural survival for different tonotopic positions along the cochlea. The neural survival status of the patient may for example be represented as an audiogram of the patient or may be determined as described in WO2021053045A1, a co-pending patent application of applicant.

The neural survival status may include any states of the neural or cochlear tissue, such as myelination, level of degeneration, functioning ion channels and the like. The neural survival status of the patient may for example specify that the patient requires electric cochlear stimulation for tonotopic positions along the cochlea (along the scala tympani) corresponding to frequencies below 1150 Hz and above 4800 Hz (and to the corresponding insertion angle range) but has normal or sufficient residual hearing and does hence not require electric cochlear stimulation for tonotopic positions along the cochlea (along the scala tympani) corresponding to frequencies between 1150 Hz and 4800 Hz (and to the corresponding insertion angle range). Determining the geometry of the electrode array may comprise determining portions along the length of the electrode array that should contain electrode contacts corresponding to the insertion angle ranges at which electric stimulation is needed by the patient. In the remaining portions along the length of the electrode array, corresponding to the insertion angle ranges at which the patient does not require electric stimulation, may be left free of any electrode contacts.

Additionally or alternatively, determining the geometry of the electrode array may comprise determining the position of one or more electrode contacts of the electrode array along the electrode array based on the computed predicted arrangement of the electrode array within the cochlea of the patient and on one or more stimulation frequencies of a speech processor connectable to the one or more stimulation electrodes. As a result, the electrode contacts may be distributed along the electrode array with spacings between contiguous electrode contacts that vary along the length of the electrode array, i.e. with non-constant spacing, and are adapted to the specific tonotopic stimulation requirements of the patient and to the stimulation frequencies of the speech processor connected to the electrode array. This may allow combining the information about the frequencies at which the speech processor may provide stimulation with the tonotopic positions of the patient in view of the patient-specific cochlear anatomy reflected in the predicted arrangement of the electrode array computed according to the invention. This may result in reduced pitch mismatch and better speech performance.

The tonotopic frequency distribution along the cochlea of the patient may be mathematically modelled, taking into account the patient-specific cochlear anatomy reflected in the patient-specific data and/or in the predicted arrangement of the electrode array, for example using the Greenwood function derived by Greenwood in "A cochlear frequency-position function for several species—29 years later", *The Journal of the Acoustical Society of America,* 87(6):2592-2605, 1990. In particular in embodiments in which the patient-specific data about the geometry of the cochlea of the patient is volumetric data and allows a full volumetric reconstruction of the cochlea of the patient, the spiral path of the basilar membrane of the patient may be obtained from the patient-specific data for using the Greenwood function, possibly using an appropriate conversion function as was done in O. Stakhovskaya et al., "Frequency map for the human cochlear spiral ganglion: implications for cochlear implant", JARO-Journal of the Association for Research in Otolaryngology, 8(2):220-233, 2007.

As a further example, the tonotopic frequency distribution along the cochlea of the patient may be modelled based on the patient-specific data about the geometry of the cochlea of the patient and/or of a part thereof, in particular of the basilar membrane and/or of the organ of corti of the patient, for example using the empirical model presented in Helpard et al. "An Approach for Individualized Cochlear Frequency Mapping Determined From 3D Synchrotron Radiation Phase-Contrast Imaging", IEEE Trans Biomed Eng. 2021 December; 68(12):3602-3611. doi: 10.1109/TBME.2021.3080116. This allows for patient-specific cochlear implant stimulation that ensures that the electrode contacts of the electrode array provide stimulation at the correct tonotopic position along the cochlea of the.

A second aspect of the invention refers to a system for determining a target geometry of an electrode array for a cochlear implant for a patient. The system may include data processing means, such as a processor, specifically configured to implement the method according to any of the embodiments of the first aspect of the invention.

The system comprises an anatomical model module comprising patient-specific data about the geometry of the cochlea of the patient or of a part thereof; an electrode array geometry module configured to compute a predicted arrangement of the electrode array within the cochlea of the patient based on the patient-specific data about the geometry of the cochlea of the patient or of said part thereof and on a predefined geometric relation between the geometry of the cochlea of the patient and the predicted arrangement of the electrode array within the cochlea of the patient; and an electrode array design module configured to determine the target geometry of the electrode array corresponding to the predicted arrangement of the electrode array within the cochlea of the patient computed by the electrode array geometry module.

The predefined geometric relation may be defined for the system as previously defined for any of the embodiments of the method of the first aspect of the invention.

The electrode array geometry module configured to compute the predicted arrangement of the electrode array within the cochlea of the patient as described above for any of the embodiments of the method of the first aspect of the invention.

In particular, the geometry of the electrode array determined by the electrode array design module may comprise a length of the electrode array.

The anatomical model module may comprise a cochlea path module comprising patient-specific data about a spiral path of the cochlea of the patient or of a part thereof; and a cochlea area module comprising empirical data about cross-sectional areas of a human cochlea or of a part thereof perpendicular to a corresponding spiral path of the human cochlea for different insertion angles. The anatomical model module may be configured to generate the patient-specific data about the geometry of the cochlea as volumetric data based on the patient-specific data about said spiral path and on the empirical data about said cross-sectional areas.

The system may further comprise an imaging device for obtaining the patient-specific data about the geometry of the cochlea of the patient using an imaging technique, preferably computer tomography, more preferably cone beam computed tomography (CBCT).

The system may further comprise a first tonotopy module comprising patient-specific data about a neural survival status of the cochlea of the patient. The electrode array design module may further be configured to determine the geometry of the electrode array for the cochlear implant for the patient based on the patient-specific data about a neural survival status of the cochlea of the patient and the geometry of the electrode array may be determined by the electrode array design module comprising a position of one or more stimulation electrodes of the electrode array along the electrode array.

The system may further comprise a second tonotopy module, which may be the same as or be integrated with the first tonotopy module, comprising data about one or more stimulation frequencies of a speech processor connectable to the one or more stimulation electrodes. The electrode array design module may further be configured to determine the geometry of the electrode array for the cochlear implant for the patient based on the data about one or more stimulation frequencies of a speech processor connectable to the one or more stimulation electrodes. The geometry of the electrode array determined by the electrode array design module may comprise a position of one or more stimulation electrodes of the electrode array along the electrode array.

A third aspect of the invention refers to a method of manufacturing an electrode array for a cochlear implant for a patient. The method comprises determining a target geometry of the electrode array according to the method of any of the embodiments of the first aspect of the invention previously described and/or using a system according to any of the embodiments of the second aspect of the invention previously described; and manufacturing the electrode array having a geometry corresponding to the determined target geometry. As a result, a patient-specifically adapted electrode array can be manufactured.

The electrode array may be manufactured using a patient-specific mold. However, the electrode array may alternatively be manufactured using a modular mold system comprising a plurality of mold modular elements. The mold modular elements may have different width dimensions and may correspond to different cross-sectional profiles of the electrode array perpendicular to the longitudinal direction thereof. Manufacturing the electrode having the geometry corresponding to the determined target geometry may then comprise choosing an appropriate subset of mold modular elements of the plurality of mold modular elements based on the determined target geometry and using the subset of mold modular elements for manufacturing the electrode array. The use of a modular mold system can eliminate the necessity of providing a one-use patient-specific mold for every patient.

A dimension of one or more of the mold modular elements of the chosen subset of mold modular elements, preferably of each of them, for example a width thereof corresponding to a portion of the length of the electrode array to be manufactured, may correspond to a separation distance between two contiguous electrode contacts of the electrode array.

DESCRIPTION OF PREFERRED EMBODIMENTS OF THE INVENTION

Figure 1:
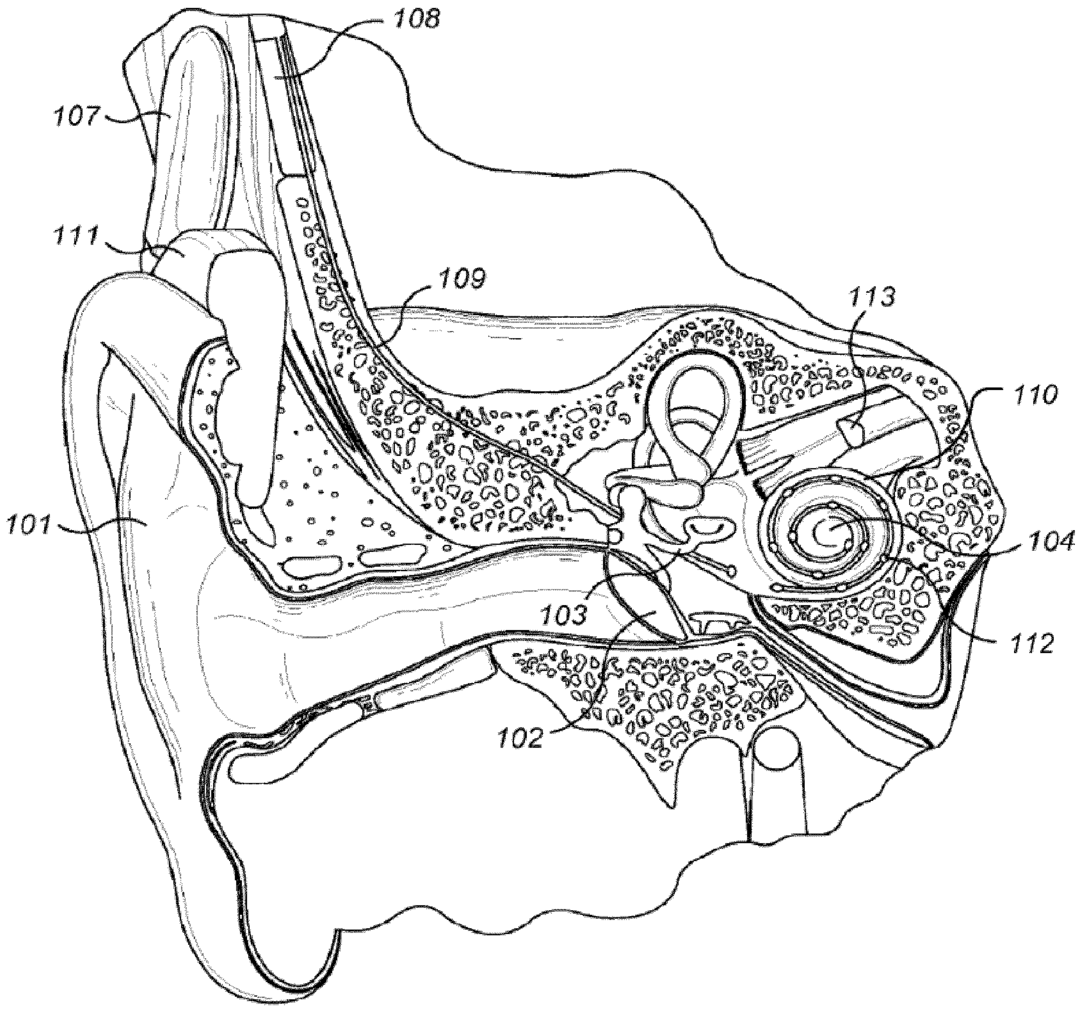
FIG. 1. shows anatomical structures of a human ear and some components of a typical cochlear implant.

For the purposes of promoting an understanding of the principles of the invention, reference will now be made to specific preferred embodiments illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to someone skilled in the art to which the invention relates within the scope defined by the claims.

FIG. 1 shows anatomical structures of a human ear and some components of a typical cochlear implant. As described above, the cochlear implant comprises a flexible elongated electrode array 110 that is inserted into the scala tympani of the cochlea 104 of the patient. The electrode array 110 comprises a plurality of electrode contacts 112 that are linearly distributed along the longitudinal dimension of the electrode array 110 and can be used for providing electrical stimulation to auditory neural tissue within the scala tympani of the patient.

Figure 2:
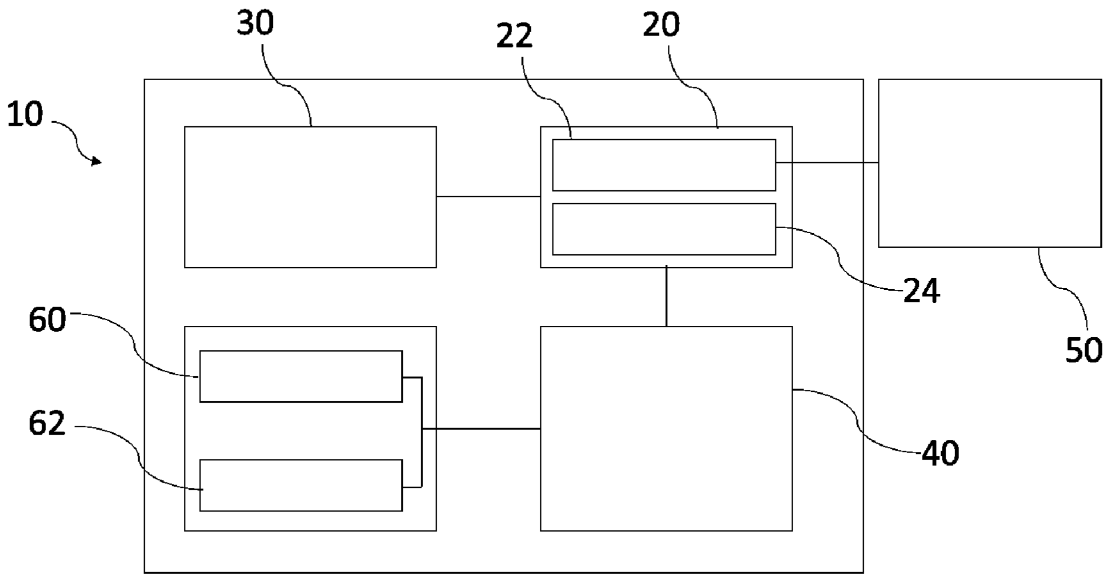
FIG. 2 shows a schematic illustration of a system for determining a target geometry of an electrode array for a cochlear implant for a patient according to an exemplary embodiment of the invention.

FIG. 2 is a schematic illustration of a system for determining a target geometry of an electrode array for a cochlear implant in a manner individually tailored to the specific requirements and anatomy of a patient. The system 10, which can be a computer-implemented method that may be hardware-based and/or software-based, comprises an anatomical model module 20, an electrode array geometry module 30 and an electrode array design module 40 that are functionally connected. Each of the modules 20, 30 and 40 can comprise data processing hardware or software components and/or data storage hardware or software components appropriate for implementing the functionalities of the invention described above and to be discussed in further detail below. In particular, the system 10 is configured for implementing a method for determining a geometry of an electrode array for a cochlear implant for a patient according to the first aspect of the invention.

In the exemplary embodiment shown in FIG. 2, the anatomical model module 20 comprises a cochlear path module 22 that is optionally connected to an imaging device 50. The imaging device 50 can be a component of the system 10 or an external imaging device. The cochlear path module 22 is configured for obtaining a representation of the lateral wall (LW) of the cochlea of the patient from one or more images of the cochlea of the patient obtained of by means of cone beam computed tomography by the imaging device 50.

Figure 3:
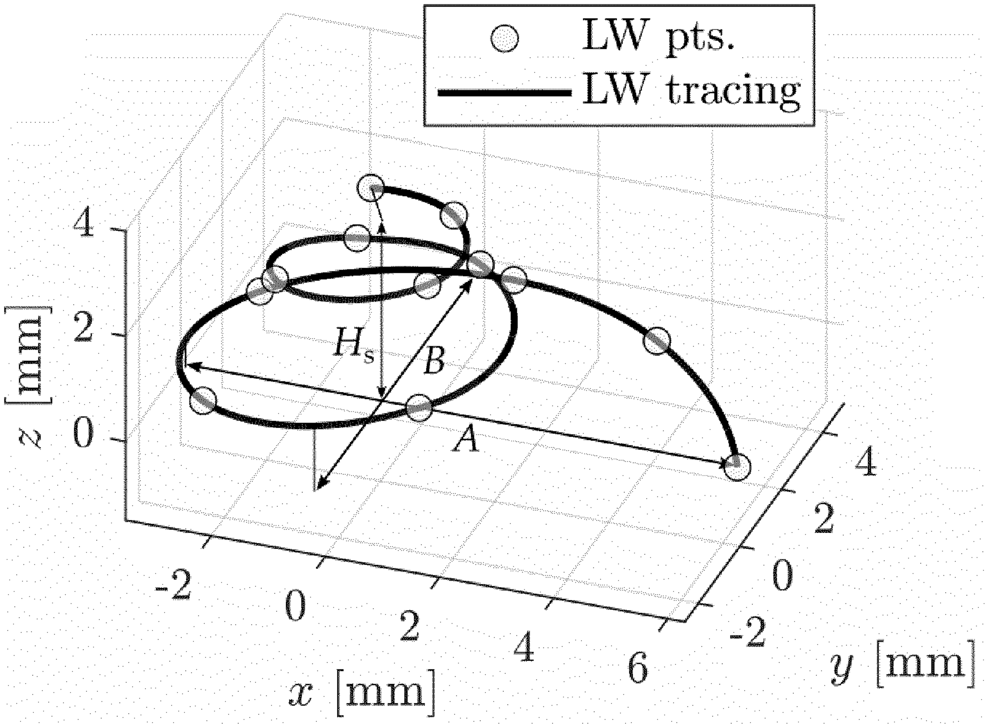
FIGS. 3-6 show schematic illustrations of steps of generating patient-specific data about the geometry of the cochlea of the patient according to an exemplary embodiment of the method of the first aspect of the invention, possibly using the system of FIG. 2.

The cochlear path module 22 can for example implement the method described in D. Schurzig et al. "Cochlea Helix and Duct Length Identification—Evaluation of Different Curve Fitting Techniques," *Cochlear Implants Int.* 19(5), pp. 268-83, 2018 to interpolate the spiral path followed by the lateral wall of the cochlea of the patient from a plurality of segmentation points, in particular using OsiriX MD. This is schematically illustrated in FIG. 3, where the segmentation points are indicated at "LW pts" and the interpolated spiral path of the lateral wall of the cochlea of the patient is indicated as "LW tracing".

The graphical representation of spiral paths of the cochlea or parts thereof in FIGS. 3, 4, 6, 8, 9 and 10 of the present application, uses the coordinate system proposed in B. M. Verbist et al. "Consensus panel on a cochlear coordinate system applicable in histologic, physiologic, and radiologic studies of the human cochlea," Otol Neurotol 31, pp. 722-30, 2010, wherein the modiolus coincides with the z-axis and the centre of the round window lies on the x axis.

Figure 4:
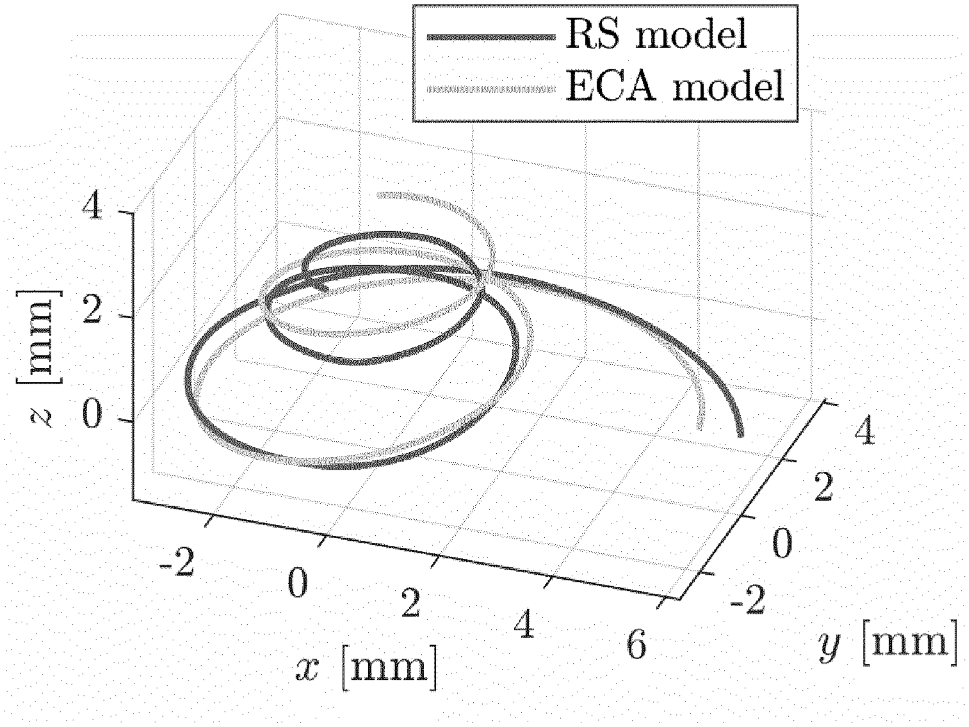

Alternatively, the cochlear path module 22 can comprise, for example stored in a data storage component, or generate, for example from CBCT images provided by the imaging device 50, patient-specific data about the spiral path of the lateral wall LW of the cochlea of the patient, for example using the elliptic-circular approximation (ECA) method discussed in D. Schurzig et al., "A Novel Method for Clinical Cochlear Duct Length Estimation toward Patient-Specific Cochlear Implant Selection", OTO open, vol. 2, no. 4, p. 2473974X18800238, 10 2018, or the so-called regression scaling (RS) model presented in D. Schurzig et al., "A Cochlear Scaling Model for Accurate Anatomy Evaluation in Cochlear Implantation," Hear Res 403: 108166, 2021. For this purpose, the required parameters A (cochlear diameter), B (cochlear width) and possibly Hs (cochlear height) of the cochlea of the patient can be obtained from the CBCT images of the cochlea of the patient received from the imaging device 50. The result is schematically illustrated in FIG. 4 both for the ECA and for RS. These approaches may be less time consuming than the above approach based on the use of OsiriX MD.

Irrespectively of the technique used for obtaining the patient-specific data, patient-specific data about the spiral path of the lateral wall LW of the cochlea of the patient is available in the cochlear path module 22.

Figure 5:
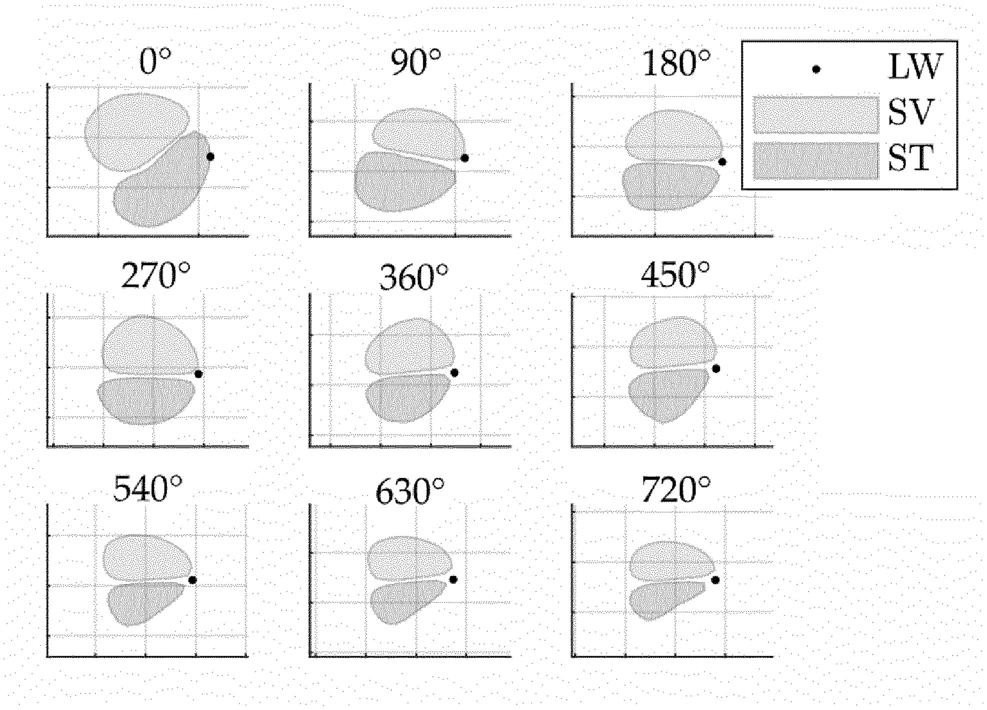

The anatomical model module 20 further comprises a cochlear area module 24 that comprises, in particular stored in a corresponding data storage component and/or received by a corresponding data processing component, empirical data about cross-sectional area of the human cochlea, for example averaged over a given test population, of the scala tympani and the scala vestibuli in planes perpendicular to the corresponding spiral path of the lateral wall of the human cochlea (possibly also obtained as an average over the test population) for different insertion angles. FIG. 5 shows a schematic graphic representation of the cross sections of the scala vestibuli SV and the scala tympani ST as well as of a position of the lateral wall LW of the cochlea in the corresponding cross-sectional plane for different insertion angles along the cochlea according to the empirical data comprised in the cochlear area module 24.

Figure 6:
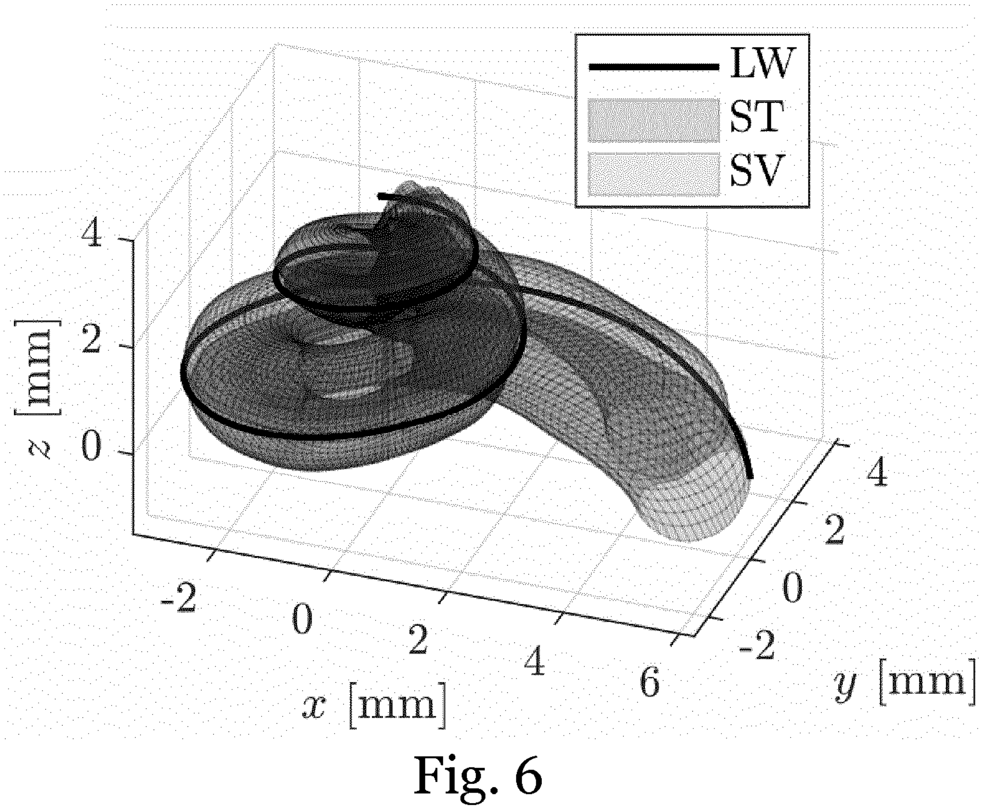

The anatomical model module 20 is configured to combine the patient-specific data about the spiral path of the lateral wall LW of the cochlea of the patient (cf. FIG. 3 or 4), that is for example obtained based on real CBCT images provided by the imaging device 50, with the empirical (non-patient-specific) data about the cross-sectional areas of a modelled human cochlea (cf. FIG. 5) to generate volumetric data representing the full volume of the scala tympani and the scala vestibuli of the patient in 3D space, as shown in FIG. 6. This is a modelled representation of the geometry of the scala vestibuli and the scala tympani of the patient based on the patient-specific data about the spiral path of the lateral wall LW of the cochlea of the patient that reflects the patient-specific cochlea anatomy.

The electrode array geometry module 30 is configured to compute a predicted arrangement of the electrode array of the cochlear implant within the scala tympani of the patient from the patient-specific model of the geometry of the cochlea of the patient encoded in the patient-specific data about the geometry of the cochlea of the patient (cf. FIG. 6) using a predefined geometric relation.

For example, the electrode array geometry module 30 may be configured to assume that a centre-line of the electrode array, when received within the scala tympani of the patient, will follow a spiral path separated a constant distance, for example 0.35 mm, from the outer internal wall of the scala tympani of the patient, i.e. from the internal wall of the scala tympani of the patient distal from the modiolus. Thereby, a predicted arrangement of the electrode array within the cochlea of the patient can be obtained (computed) by the electrode array geometry module 30 patient-specific data about the geometry of the cochlea of the patient.

Figure 7:
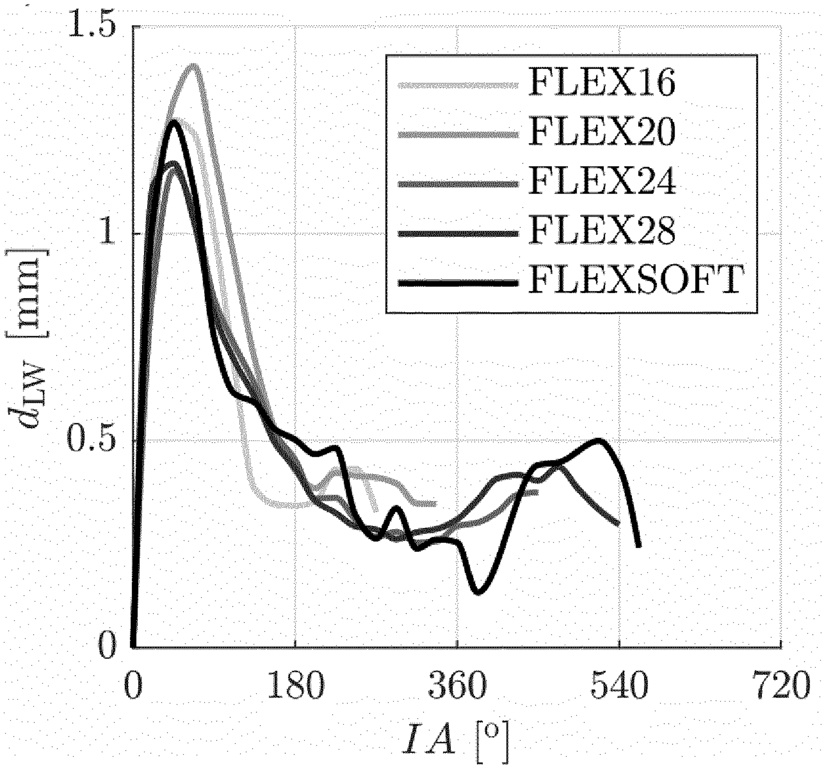
FIG. 7-10 show schematic illustrations of steps of computing a predicted arrangement of the electrode array within the cochlea of the patient according to an exemplary embodiment of the method of the first aspect of the invention, possibly using the system of FIG. 2.

In other exemplary embodiments, the electrode array geometry module can be configured to compute the predicted arrangement of the electrode array within the scala tympani of the patient from the patient-specific data using a function $d_{LW}$(IA) representing a functional dependence of a distance $d_{LW}$ between the lateral wall LW of the cochlea of the patient and a location of a test electrode array within the scala tympani of a model human cochlea in a horizontal direction parallel to a shortest distance from the lateral wall of the cochlea LW to the modiolus (a direction pointing towards the modiolus in the xy-plane) as a function of insertion angle IA. FIG. 7 shows different examples of such function $d_{LW}$(IA) obtained from a statistical dataset for a test population and for different types of test electrode arrays having different lengths with the electrode array type FLEX16 (length=16 mm) being the shortest, the electrode array type FLEX20 (length=20 mm) being longer than FLEX16, and so on, and the electrode array type FLEX-SOIFT (length=31.5 mm) being longest. The functions $d_{LW}$(IA) can be obtained according to the approach presented in R. Salcher et al., "On the Intracochlear Location of Straight Electrode Arrays After Cochlear Implantation: How Lateral Are Lateral Wall Electrodes?," *Otol Neurotol* 42(2), pp. 242-250, 2021.

Figure 8:
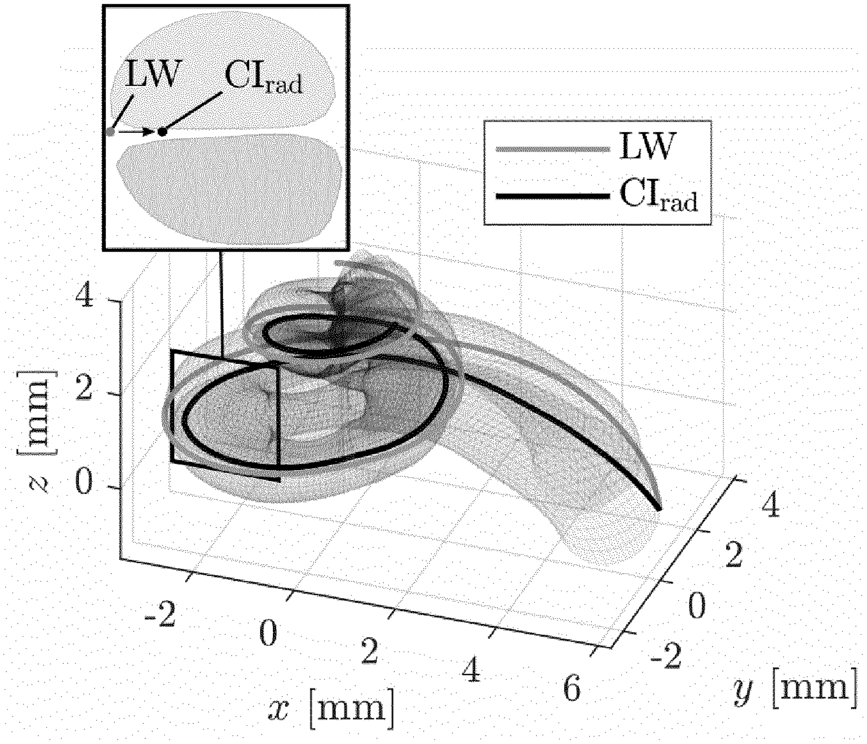
Figure 9:
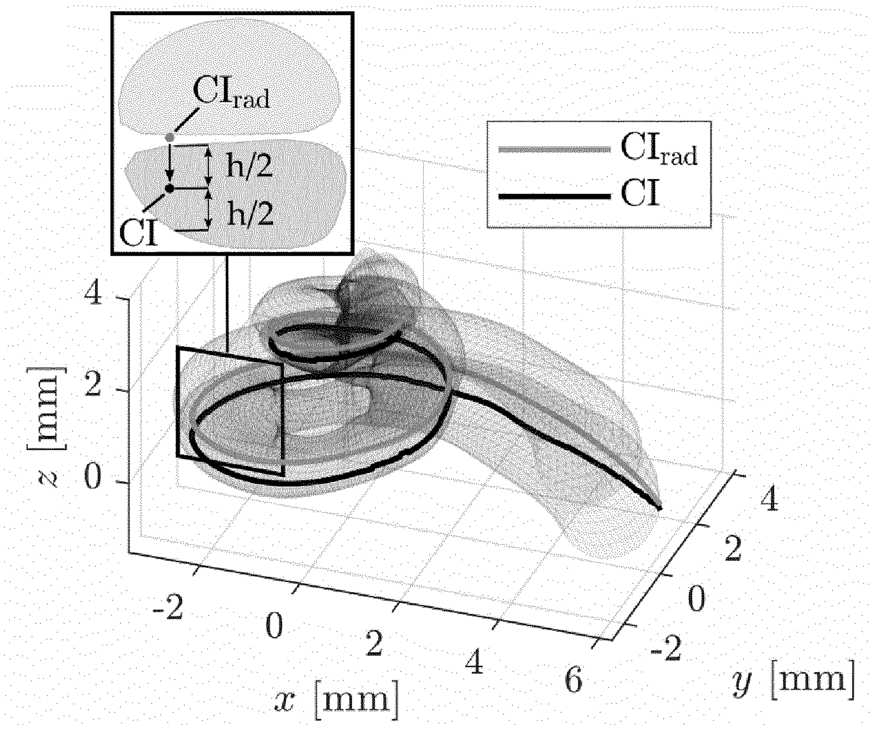

As illustrated in FIGS. 8 and 9, the electrode array geometry module 30 is configured to compute the predicted arrangement of the centre-line of the electrode array within the cochlea of the patient (with the cochlea of the patient being modelled by the patient-specific data represented in FIG. 6) by assuming that the centre-line of the electrode array (represented as a black line CI in FIG. 9) is arranged at a predetermined distance from the lateral wall LW of the cochlea of the patient in a horizontal direction perpendicular to the z direction corresponding to a direction parallel to a shortest distance from the lateral wall LW of the cochlea of the patient to the modiolus of the patient (to the x-direction in the example cross-sectional frame of FIG. 8). The predetermined distance can be taken as a distance corresponding to an appropriate one of the functions $d_{LW}$(IA) represented in FIG. 7. As a result, as schematically illustrated in FIG. 8, the position of the lateral wall LW of the cochlea of the patient is projected radially towards the modiolus of the patient to a position $CI_{rad}$. A distance between the position $CI_{rad}$ and lateral wall LW in the x-direction is defined by the corresponding predefined geometric relation $d_{LW}$(IA).

Further, as schematically illustrated in FIG. 9, the electrode array geometry module 30 is configured to assume that the centre-line of the electrode array is arranged within the scala tympani of the patient at the radial position $CI_{rad}$ (cf.

FIG. 8) and at a vertical position (a position in the z-direction) corresponding to ½ of the height of the scala tympani of the patient at said radial position $CI_{rad}$ (see FIG. 9). However, other fractions of the height of the scala tympani of the patient can be used in other examples, not necessarily ½. The height of the scala tympani of the patient is understood herein as a separation distance between the upper sidewall of the scala tympani, which is adjacent to the scala vestibuli, and a lower sidewall of the scala tympani, located opposite the upper sidewall in the vertical direction z.

Using the patient-specific data provided by the anatomical model module 20 and the predefined geometric relation, the electrode array geometry module 30 computes a predicted arrangement CI of the electrode array, in particular of a centre-line of thereof, when received within the cochlea of the patient, see FIG. 9.

Figure 10:
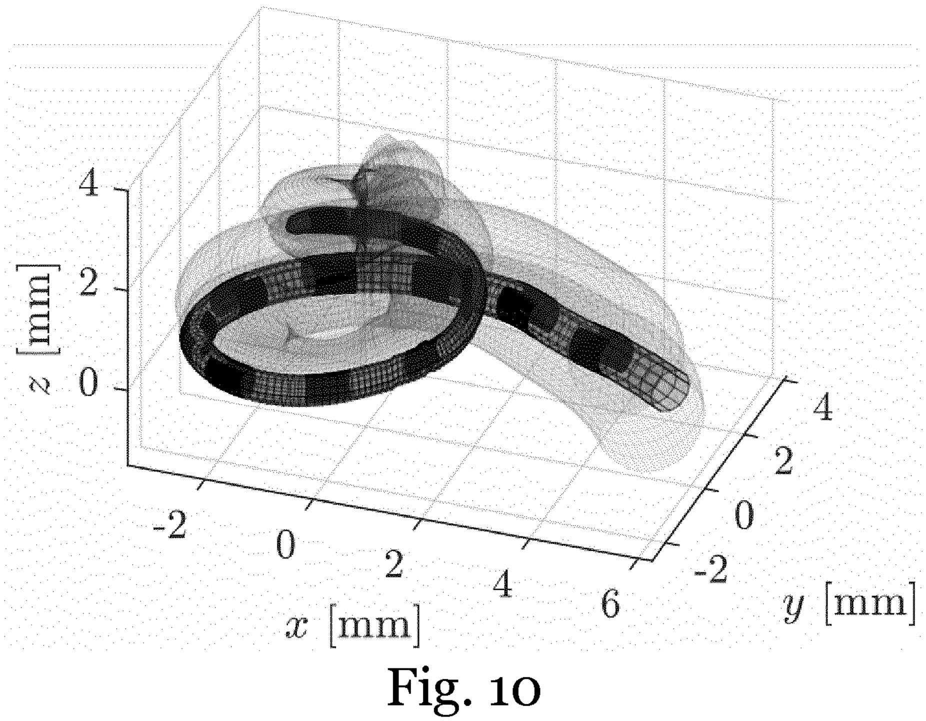

As shown in FIG. 10, the electrode array geometry module 30 can further be configured to incorporate cross-sectional information about the electrode array in order to compute not only the predicted arrangement of the centre-line of the electrode array illustrated in FIG. 9, but the entire volumetric distribution of the electrode array within the cochlea of the patient.

The system 10 further comprises a first tonotopy module 60 and a second tonotopy module 62, which in the exemplary embodiment shown in FIG. 1 are integrated within a single module component. The first tonotopy module 60 comprises patient-specific data about a neural survival status of the cochlea of the patient. Such patient-specific data about the neural survival starters of the cochlea of the patient can for example correspond to the audiogram represented in FIG. 11, corresponding to a graphical representation of a neural hearing ability of the patient for different sound frequencies. Using the patient-specific data about the neural survival status of the cochlea of the patient comprised in the first tonotopy module 60, for example stored in a data storage component thereof, the electrode array design module 40 can determine an optimal length of the electrode array 110 and/or and optimal position of a plurality of electrode contacts 112 distributed along the electrode array 110 (see electrode array depicted in FIG. 13). This is explained in further detail below.

Further, the second tonotopy module 62 comprises data about one or more stimulation frequencies of a speech processor connected or connectable to the electrode contacts 112 of the electrode array 110 for providing stimulation. The second tonotopy module 62 can receive this information from the speech processor itself. The electrode array design module 40 can use the patient-specific data about the neural survival status of the cochlea of the patient comprised in the first tonotopy module 60 and the data about the stimulation frequencies of the speech processor comprised (or received via) the second tonotopy module 62 to determine an ideal position of each of the electrode contacts 112 along the electrode array 110 so as to optimise tonotopic matching, i.e. such that the locations of the electrode contacts 112 along the electrode array 110 are such that, when the electrode array is received within the cochlea of the patient, the speech processor can provide stimulation with each given stimulation frequency at a location (insertion angle) within the scala tympani of the patient that corresponds to a location in which such frequency is naturally perceived.

Figure 11:
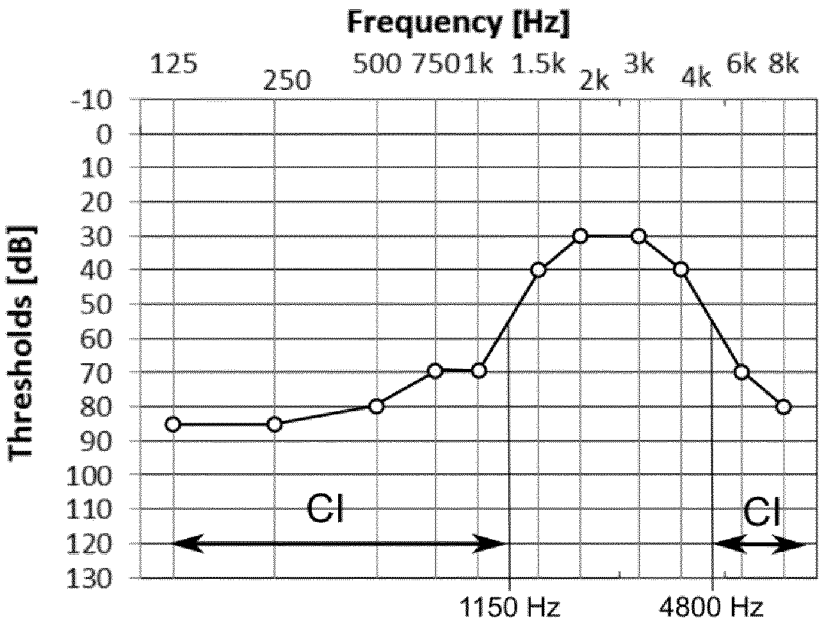
FIG. 11 shows an audiogram representing a neural survival status of a patient.

For example, the audiogram of the patient represented in FIG. 11 indicates that the patient requires electric stimulation for frequencies below 1150 Hz and above 4800 Hz but does not require stimulation for intermediate frequencies from 1150 Hz to 4800 Hz. Accordingly, the electrode array design module 40 can determine that the electrode contacts 112 are to be arranged along a first portion L1 of the electrode array 110 corresponding to frequencies from 125 Hz to 1150 Hz and along a second portion L2 of the electrode array 110 corresponding to frequencies from 4800 Hz to 8500 Hz (see FIG. 13), whereas no electrodes need to be arranged between the portions L1 and L2, since the patient does not require stimulation at the corresponding frequencies. For another patient that should for example require stimulation only up to a frequency of 3000 Hz, an electrode array with a shorter length and/or a different distribution of the electrode contacts 112 could be used. Thus, the electrode array design module 40 would then determine a shorter geometry for the electrode array 110 and the corresponding arrangement of the electrode contacts 112 along the electrode array 110.

Thus, the system 10 allows determining the ideal geometry of an electrode array 110 for taking into account the specific individual requirements and anatomy of a given patient. For example, optimised target positions for each of 12 electrode contacts E1-E12 (cf. electrode contacts 112 in FIG. 13) to be arranged on an electrode array 110 for providing stimulation at respective frequencies 149 Hz (E1), 261 Hz (E2), 408 Hz (E3), 601 Hz (E4), 854 Hz (E5), 1191 Hz (E6), 1638 Hz (E7), 2233 Hz (E8), 3028 Hz (E9), 4090 Hz (E10), 5610 Hz (E11) and 7412 Hz (E12). For conventional electrodes in Table 1, which represents the respective distances of each of the electrodes E1 to E12 from the tip of the standard electrode array for different standard-lengths of the electrode array.

TABLE 1

| Array length | Electrode contact positions (distance from electrode tip in mm) | | | | | | | | | | | |
|---|---|---|---|---|---|---|---|---|---|---|---|---|
| (mm) | E1 | E2 | E3 | E4 | E5 | E6 | E7 | E8 | E9 | E10 | E11 | E12 |
| 31.5 | 2.4 | 4.6 | 6.7 | 8.8 | 10.8 | 12.8 | 14.7 | 16.7 | 18.7 | 20.6 | 22.7 | 24.6 |
| 28 | 1.6 | 3.6 | 5.5 | 7.4 | 9.2 | 11.0 | 12.8 | 14.5 | 16.3 | 18.1 | 20.0 | 21.7 |
| 24 | 1.1 | 2.8 | 4.5 | 6.1 | 7.7 | 9.2 | 10.8 | 12.3 | 13.9 | 15.4 | 17.1 | 18.6 |
| 20 | −0.3 | 1.3 | 2.7 | 4.2 | 5.6 | 6.9 | 8.3 | 9.7 | 11.1 | 12.4 | 13.9 | 15.2 |

The values of the Table 1 are calculated using the equation:

$$DE = x - (TL - EL)$$

wherein DE is the distance of a given electrode from the tip of the electrode array, EL is the length of the electrode array, TL is the length of the basilar membrane of the patient (which was assumed to be 33 mm for EL=31.5 mm, 30 mm for EL=28 mm, 26 mm for EL=24 mm and 23 mm for EL=20 mm in the examples of Table 1) and x is a position along the basilar membrane of the patient related to the frequency, i.e. the perceived pitch, by the Greenwood function:

$$F = A(10^{ax} - k) \rightarrow x = \log_{10}(F/A + k)/a,$$

where F is the frequency expressed in Hz, and A, k and a are coefficients, which for humans have values A=165.4; a=2.1 and k=0.88. The geometry of the basilar membrane of the patient, in particular the length thereof TL, can be obtained as a patient-specific empirical parameter from the volumetric reconstruction of the cochlea of the patient encoded in the patient-specific data about the geometry of the cochlea of the patient.

Compared to conventional electrodes with constant electrode contact spacing as listed in Table 1, an electrode array designed according to the present invention may have non-constant spacing between contiguous electrode contacts. Such positions of the electrode contacts on the electrode array according to the present invention can be determined based on the real anatomy of the cochlea of the patient provided by the patient-specific data and taking into account the tonotopy, for example as described by the Greenwood function or by a related function. In a further embodiment, the electrode contact positions may be based on the neural survival status of the cochlea of the patient receiving the electrode array. Because the electrode is tailored for the individual patient cochlear, an optimal electrode contact to pitch-percept can be obtained and imperfect matches, such as for example for electrode contact E1, as shown in Table 1, for the electrode having a standard electrode array length of 20 mm do no longer occur. In this exemplary case, in order for an optimal frequency-to-electrode contact position match for the standard electrode array, electrode contact E1 would need to lie 0.3 mm outside the standard electrode array in front of the tip, which is represented by the minus-sign in Table 1.

As a further example, the empirical expression for the stimulation frequency F used in Helpard et al. "An Approach for Individualized Cochlear Frequency Mapping Determined From 3D Synchrotron Radiation Phase-Contrast Imaging", IEEE Trans Biomed Eng. 2021 December; 68(12):3602-3611. doi: 10.1109/TBME.2021.3080116 can be used:

$$F = 2^{\frac{m\theta+168+c}{12}}; \text{ with}$$

$$m = 0.0285N - 0.1978; \text{ and}$$

$$c = -1.26 - 2.33\cos(0.0059\,\theta) - 6.84\sin(0.0059\,\theta);$$

wherein N represents the number of turns of the basilar membrane of the patient and θ represents the maximal insertion angle of the patient measured from the centre of the round window (if θ is expressed in degrees). In one example, N may be calculated using the equation N=θ/360, which can be considered a good approximation. However other ways to calculate N as apparent to the skilled-in-the art may be used and by way of example are explained more fully below.

This expression can be used for determining the required position of each electrode contact 112 along the electrode array 110, such that each electrode contact 112 provides stimulation at the appropriate tonotopic position along the scala tympani of the patient. This angle-based approach has the practical advantage, in particular over length-based approaches relying on the Greenwood function, not necessarily having to estimate or measure the length of the basilar membrane of the patient and/or of the lateral wall of the cochlea of the patient. The length of the basilar membrane of the patient may be difficult to measure in practice from CT images such as CBCT images due to possible poor anatomical detail and/or due to lack of soft tissue contrast in such images. Further, estimations of the length of the basilar membrane from a measurement or calculation of the length of the lateral wall may not accurately reflect the specific anatomy of the patient. In contrast, an estimation of the angular parameters N and 6 based on the geometry of the cochlea of the patient reflected by the patient-specific data about the geometry of the cochlea of the patient, for example obtained from the patient-specific data about the spiral path of the lateral wall LW of the cochlea of the patient (cf. FIG. 3 or 4) and/or from volumetric data representing the full volume of the scala tympani of the patient (cf. FIG. 6), may provide improved accuracy and reliability and hence improved performance of the cochlear implant.

Figure 12:
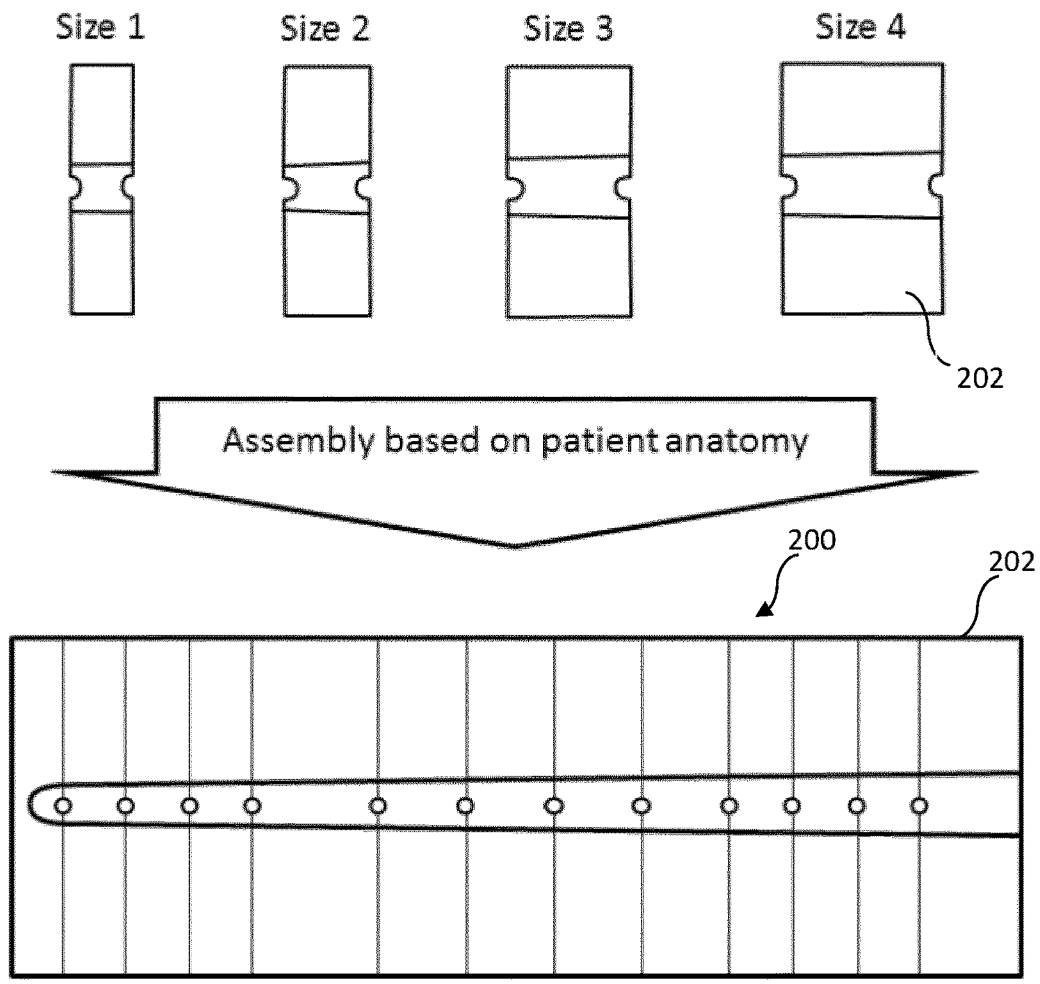
FIG. 12 shows a schematic illustration of a modular mold system for manufacturing an electrode array according to an exemplary embodiment of the method of the third aspect of the invention.

FIG. 12 is a schematic illustration of a modular mold system 200 for manufacturing an electrode array 100 having a geometry determined according to the method of the present invention, for example by the system 10 of FIG. 2. The modular mold system 200 comprises a plurality of mold modular elements 202 having different dimensions, in particular different widths, wherein the electrode array 110 is to be manufactured along the width of the mold modular elements 202, as illustrated in FIG. 12. The mold modular elements 202 are configured for forming different sections of the electrode array 110 having a corresponding cross-sectional profile, possibly taking into account a tapered profile of the electrode array 110, as is the case in the exemplary embodiment illustrated in FIG. 12. Four different types of mold modular element 202 are exemplarily shown in FIG. 12 ("Size1", "Size2", "Size3" and "Size4"). However, the number of different types of mold modular element 202 and/or the overall number of mold modular elements 202 is not limited to four and may be greater or smaller.

Once a target geometry of an electrode array has been determined according to the present invention, a corresponding subset of the mold modular elements 202 can be chosen in view of the target geometry. As illustrated in FIG. 6, a width of each of the mold modular components 202 of the chosen subset (and possibly also shape and size of a corresponding recess for forming a cross section of the electrode array included in each mold modular component 202) can be chosen to correspond to a separation distance between contiguous electrode contacts of the electrode array according to the geometry determined according to the invention. The modular system 200 eliminates the necessity of providing a patient-specific mold for each individual patient.

Figure 13:
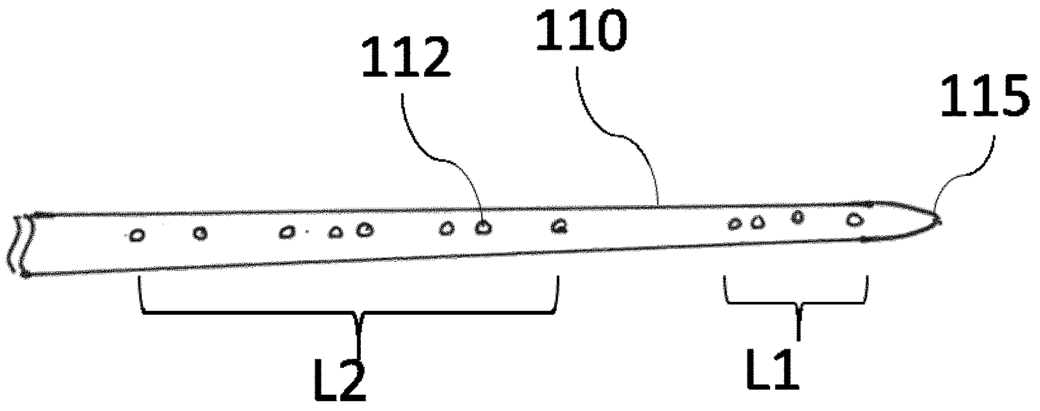
FIG. 13 shows a schematic illustration of an electrode array manufactured according to an exemplary embodiment of the method of the third aspect of the invention

FIG. 13 shows an electrode array 110 manufactured according to the invention and having a corresponding length and distribution of the electrode contacts 112, for example a distribution at positions such that, when the electrode array 110 is inserted into the scala tympani of the patient, the electrode contacts 112 are arranged at corresponding tonotopic positions computed as explained above using the length-based Greenwood function and/or the angle-based function presented by Helpard et al. In a further embodiment, the electrode contact 112 positions and distances may be computed, at least in part based on the empirical equation for the spiral ganglion cells (SGC) according O. Stakhovskaya, D. Sridhar, B. H. Bonham, and P. A. Leake. "Frequency map for the human cochlear spiral ganglion: implications for cochlear implants." JARO-Journal of the Association for Research in Otolaryngology, 8(2):220-233, 2007:

$$y = \frac{100}{1 + \left(A * \frac{100}{x} + B * \frac{x}{100} - A - B\right)^2}$$

wherein x is the position on the basilar membrane relating to a frequency F and y the position for the same frequency F on the spiral ganglion and A and B are empirical parameters. Typically, A=0.22 and B=−0.93, however it is understood that A and B can take different empirical values, dependent on the group of patients the recipient patient can be attributed. In one exemplary embodiment, the electrode contact 112 positions and distances may be computed at least in part based on the tonotopy-mapping y for the spiral ganglion cells for the basal part of the electrode array 110 and at least in part based on the tonotopy for the basilar membrane x in the distal part to the electrode array 110. The length of the basal part is based on the patient-data and may be in the range from 9 mm to 15 mm, typically 13.7 mm long. The distal part is contiguous to the basal part and extends for the remaining length of the electrode array 112 until up to the tip.

Although preferred exemplary embodiments are shown and specified in detail in the drawings and the preceding specification, these should be viewed as purely exemplary and not as limiting the invention. It is noted in this regard that only the preferred exemplary embodiments are shown and specified, and all variations and modifications should be protected that presently or in the future lie within the scope of protection of the invention as defined in the claims.

The invention claimed is:

1. A method for determining a geometry of an electrode array for a cochlear implant for a patient comprising:

computing a predicted arrangement of the electrode array within the cochlea of the patient based on patient-specific data about the geometry of the cochlea of the patient or of a part thereof and on a predefined geometric relation between the geometry of the cochlea of the patient or of a part thereof and the predicted arrangement of the electrode array when received within the cochlea of the patient;

determining the geometry of the electrode array based on the computed predicted arrangement of the electrode array within the cochlea of the patient; and generating the patient-specific data about the geometry of the cochlea of the patient as volumetric data based on patient-specific data about a spiral path of the cochlea of the patient or of a part thereof and on empirical data about cross-sectional areas of a human cochlea or of a part thereof perpendicular to a corresponding spiral path of the human cochlea for different insertion angles.

2. The method of claim 1, wherein determining the geometry of the electrode array comprises determining a length of the electrode array.

3. The method of claim 1, further comprising obtaining the patient-specific data about the geometry of the cochlea of the patient using an imaging technique.

4. The method of claim 1, wherein the predefined geometric relation corresponds to a predefined distance between a center line of the electrode array and a spiral path of the cochlea of the patient or of a part thereof.

5. The method of claim 4, wherein the predefined distance is dependent on an insertion angle.

6. The method of claim 4, wherein the predefined distance is a predefined distance between the center-line of the electrode array and a spiral path of the lateral wall of the cochlea of the patient or of an inner or outer internal wall of the scala tympani of the patient.

7. The method of claim 1, wherein the predicted arrangement of the electrode array within the cochlea of the patient is computed assuming:

that a center-line of the electrode array is arranged at a first predetermined distance from a spiral path of the cochlea of the patient or of a part thereof in a horizontal direction parallel to a shortest distance from said spiral path of the cochlea of the patient or from said part thereof to the modiolus of the patient; and that the center-line of the electrode array is arranged within the scala tympani of the patient at a second predetermined distance from the spiral path of the cochlea of the patient or of a part thereof in a vertical direction parallel to the modiolus of the patient.

8. The method of claim 7, wherein said spiral path of a part of the cochlea of the patient is a spiral path of the lateral wall of the cochlea of the patient.

9. The method of claim 7, wherein the first predetermined distance corresponds to the predefined distance between the center-line of the electrode array and the spiral path of the cochlea of the patient or of a part thereof.

10. The method of claim 7, wherein the second predetermined distance corresponds to a predetermined fraction of a separation distance between an upper sidewall of the scala tympani of the patient adjacent to the scala vestibuli and a lower sidewall of the scala tympani opposite said upper sidewall of the scala tympani in said vertical direction.

11. The method of claim 1, wherein determining the geometry of the electrode array comprises determining a position of one or more electrode contacts of the electrode array along the electrode array based on the computed predicted arrangement of the electrode array within the cochlea of the patient and based on patient-specific data about a neural survival status of the cochlea of the patient.

12. The method of claim 1, wherein determining the geometry of the electrode array comprises determining a position of one or more electrode contacts of the electrode array along the electrode array based on the computed predicted arrangement of the electrode array within the cochlea of the patient and on one or more stimulation frequencies of a speech processor connectable to the one or more electrode contacts.

13. A system for determining a target geometry of an electrode array for a cochlear implant for a patient comprising:

an anatomical model module comprising patient-specific data about the geometry of the cochlea of the patient or of a part thereof;

a cochlea path module comprising patient-specific data about a spiral path of the cochlea of the patient or of a part thereof;

a cochlea area module comprising empirical data about cross-sectional areas of a human cochlea or of a part thereof perpendicular to a corresponding spiral path of the human cochlea for different insertion angles;

an electrode array geometry module configured to compute a predicted arrangement of the electrode array when received within the cochlea of the patient based on the patient-specific data about the geometry of the cochlea of the patient or of said part thereof and on a predefined geometric relation between the geometry of the cochlea of the patient and the predicted arrangement of the electrode array within the cochlea of the patient; and an electrode array design module configured to determine the target geometry of the electrode array corresponding to the predicted arrangement of the electrode array within the cochlea of the patient computed by the electrode array geometry module, wherein the anatomical model module is configured to generate the patient-specific data about the geometry of the cochlea as volumetric data based on the patient-specific data about said spiral path and on the empirical data about said cross-sectional areas.

14. The system of claim 13, wherein the geometry of the electrode array determined by the electrode array design module comprises a length of the electrode array.

15. The system of claim 13, further comprising an imaging device for obtaining the patient-specific data about the geometry of the cochlea of the patient using an imaging technique.

16. The system of claim 13, further comprising a first tonotopy module comprising patient-specific data about a neural survival status of the cochlea of the patient;

wherein the electrode array design module is further configured to determine the geometry of the electrode array for the cochlear implant for the patient based on the patient-specific data about a neural survival status of the cochlea of the patient, and wherein the geometry of the electrode array determined by the electrode array design module comprises a position of one or more electrode contacts of the electrode array along the electrode array.

17. The system of claim 13, further comprising a second tonotopy module comprising data about one or more stimulation frequencies of a speech processor connectable to the one or more electrode contacts;

wherein the electrode array design module is further configured to determine the geometry of the electrode array for the cochlear implant for the patient based on the data about one or more stimulation frequencies of a speech processor connectable to the one or more electrode contacts, and wherein the geometry of the electrode array determined by the electrode array design module comprises a position of one or more electrode contacts of the electrode array along the electrode array.

18. A method of manufacturing an electrode array for a cochlear implant for a patient comprising:

determining a target geometry of the electrode array according to the method of claim 1 and/or using a system according to claim 14; and manufacturing the electrode array having a geometry corresponding to the determined target geometry.

19. The method of claim 18, wherein the electrode array is manufactured using a modular mold system comprising a plurality of mold modular elements, wherein manufacturing the electrode having the geometry corresponding to the determined target geometry comprises choosing a subset of mold modular elements of the plurality of mold modular elements based on the determined target geometry and using the subset of mold modular elements for manufacturing the electrode array.

20. The method of claim 19, wherein a dimension of one or more of the mold modular elements of the chosen subset of mold modular elements, corresponds to a separation distance between two contiguous electrode contacts of the electrode array.

* * * * *